United States Patent
Kulkarni (10) Patent No.: US 9,302,106 B2
(45) Date of Patent: Apr. 5, 2016

(54) INTRANEURAL STIMULATION SYSTEMS AND METHODS

(75) Inventor: Abhijit Kulkarni, Newbury Park, CA (US)

(73) Assignee: Advanced Bionics AG, Staefa (CH)

( * ) Notice: Subject to any disclaimer, the term of this patent is extended or adjusted under 35 U.S.C. 154(b) by 0 days.

(21) Appl. No.: 14/390,380

(22) PCT Filed: Apr. 6, 2012

(86) PCT No.: PCT/US2012/032563
§ 371 (c)(1),
(2), (4) Date: Oct. 2, 2014

(87) PCT Pub. No.: WO2013/151559
PCT Pub. Date: Oct. 10, 2013

(65) Prior Publication Data
US 2015/0045844 A1  Feb. 12, 2015

(51) Int. Cl.
*A61N 1/00* (2006.01)
*A61N 1/36* (2006.01)
*A61B 5/04* (2006.01)
*A61B 5/12* (2006.01)
*A61N 5/06* (2006.01)
*A61N 1/05* (2006.01)
*A61N 1/372* (2006.01)

(52) U.S. Cl.
CPC ........ *A61N 1/36032* (2013.01); *A61B 5/04001* (2013.01); *A61B 5/125* (2013.01); *A61N 1/3606* (2013.01); *A61N 1/36132* (2013.01); *A61N 1/36185* (2013.01); *A61N 5/0622* (2013.01); *A61N 1/0526* (2013.01); *A61N 1/37235* (2013.01)

(58) Field of Classification Search
CPC ............ A61N 1/0541; A61N 1/36032; A61N 1/3606; A61N 1/36185; A61B 5/0408; A61B 5/04001; A61B 5/6877; A61B 2562/0209; A61B 2562/046
See application file for complete search history.

(56) References Cited

U.S. PATENT DOCUMENTS

| 4,063,048 | A | 12/1977 | Kissiah, Jr. |
| 5,515,848 | A | 5/1996 | Corbett, III et al. |
| 7,941,202 | B2 | 5/2011 | Hetke et al. |
| 7,991,475 | B1 | 8/2011 | Tang et al. |
| 2009/0143840 | A1* | 6/2009 | Middlebrooks .... A61N 1/36032 607/57 |
| 2011/0172725 | A1* | 7/2011 | Wells ................. A61N 1/36017 607/3 |

FOREIGN PATENT DOCUMENTS

| WO | WO-2007/092319 | 8/2007 |
| WO | WO-2008/010647 | 1/2008 |
| WO | WO-2010/035149 | 4/2010 |

OTHER PUBLICATIONS

International Search Report and Written Opinion received in International Application No. PCT/US12/032563, dated Dec. 18, 2012.

* cited by examiner

*Primary Examiner* — Robert N Wieland
(74) *Attorney, Agent, or Firm* — ALG Intellectual Property, LLC (57) ABSTRACT

An exemplary intraneural stimulation system may include an auditory prosthesis configured to be implanted within a patient, an intracochlear electrode array communicatively coupled to the auditory prosthesis and configured to be inserted into a cochlea of the patient, and an intraneural electrode array communicatively coupled to the auditory prosthesis and configured to be inserted into an auditory nerve of the patient. In this configuration, the auditory prosthesis may stimulate the auditory nerve by applying electrical stimulation by way of the intracochlear electrode array and/or the intraneural electrode array.

21 Claims, 9 Drawing Sheets

INTRANEURAL STIMULATION SYSTEMS AND METHODS

BACKGROUND INFORMATION

The sense of hearing in human beings involves the use of hair cells in the cochlea that convert or transduce audio signals into auditory nerve impulses. Hearing loss, which may be due to many different causes, is generally of two types: conductive and sensorineural. Conductive hearing loss occurs when the normal mechanical pathways for sound to reach the hair cells in the cochlea are impeded. These sound pathways may be impeded, for example, by damage to the auditory ossicles. Conductive hearing loss may often be helped by the use of conventional hearing aids that amplify sound so that audio signals reach the cochlea and the hair cells. Some types of conductive hearing loss may also be treated by surgical procedures.

Sensorineural hearing loss, on the other hand, is caused by the absence or destruction of the hair cells in the cochlea which are needed to transduce acoustic signals into auditory nerve impulses. People who suffer from sensorineural hearing loss may be unable to derive significant benefit from conventional hearing aid systems, no matter how loud the acoustic stimulus is. This is because the mechanism for transducing sound energy into auditory nerve impulses has been damaged. Thus, in the absence of properly functioning hair cells, auditory nerve impulses cannot be generated directly from sounds.

To overcome sensorineural hearing loss, numerous cochlear implant systems have been developed. Cochlear implant systems bypass the hair cells in the cochlea by presenting electrical stimulation to the auditory nerve fibers by way of one or more channels formed by an array of electrodes implanted in the cochlea. Stimulation of the auditory nerve fibers leads to the perception of sound in the brain and at least partial restoration of hearing function.

Unfortunately, conventional cochlear implant systems cannot present a full spectrum of audible sound to the patient. For example, there are often sounds that have pitches lower than those which can be conventionally generated by applying electrical stimulation to one or more electrodes disposed within the cochlea of a patient. This is especially the case when ossification, malformations within the cochlea, and/or other anatomical anomalies prevent full insertion and/or function of an electrode lead within the cochlea.

Intraneural stimulation has been proposed as an alternative to intracochlear stimulation that may facilitate better representation of relatively low frequencies and finer spectral resolution throughout the entire hearing spectrum. In intraneural stimulation, an electrode array is inserted into the auditory nerve (e.g., at the base of the cochlea). Individual electrode contacts disposed on the electrode array may then be used to directly stimulate individual nerve fibers included in the auditory nerve, thereby allowing an intraneural stimulation system to convey a full spectrum of audible sound to the patient.

Unfortunately, however, the nerve fibers within the auditory nerve are arranged in a helical fashion such that a transverse section of the of the auditory nerve will not represent a monotonic organization of pitch. Hence, an electrode array that has been inserted into the auditory nerve would result in non-monotonic pitch percepts when its electrode contacts are stimulated sequentially from one end of the array to the other. This makes it difficult to fit an intraneural stimulation system to a patient (i.e., determine which electrode contacts correspond to which frequencies). The fitting difficulty is exacerbated if the patient is incapable of providing subjective feedback during a fitting session (e.g., if the patient is a child).

BRIEF DESCRIPTION OF THE DRAWINGS

The accompanying drawings illustrate various embodiments and are a part of the specification. The illustrated embodiments are merely examples and do not limit the scope of the disclosure. Throughout the drawings, identical or similar reference numbers designate identical or similar elements.

DETAILED DESCRIPTION

Intraneural stimulation systems and methods are described herein. As will be described below, an intraneural stimulation system may include an auditory prosthesis configured to be implanted within a patient, an intracochlear electrode array communicatively coupled to the auditory prosthesis and configured to be inserted into a cochlea of the patient, and an intraneural electrode array communicatively coupled to the auditory prosthesis and configured to be inserted into an auditory nerve (also referred to as a cochlear nerve) of the patient. In this configuration, the auditory prosthesis may stimulate the auditory nerve by applying electrical stimulation by way of the intracochlear electrode array and/or the intraneural electrode array.

By including both an intracochlear electrode array and an intraneural electrode array in an intraneural stimulation system, various benefits to the intraneural stimulation patient may be realized. For example, dual electrode arrays (i.e., an intracochlear electrode array and an intraneural electrode array) may facilitate objective and/or automatic fitting of the intraneural stimulation system to the patient. To illustrate, a fitting system may automatically generate a frequency map for the intraneural electrode array (i.e., determine which intraneural electrode contacts disposed on the intraneural electrode array correspond to which frequencies) by directing the auditory prosthesis to apply electrical stimulation by way of an intracochlear electrode contact disposed on the intracochlear electrode array, identifying at least one intraneural electrode contact that detects an evoked response that occurs in response to the application of the electrical stimulation, and designating the identified at least one intraneural electrode contact as being correlated with the intracochlear electrode contact. This process may be repeated for each intracochlear electrode contact disposed on the intracochlear electrode array. The fitting system may then determine which frequencies correspond to each of the identified electrode contacts based on the determined correlations.

Dual electrode arrays may also facilitate improved performance of an intraneural stimulation system compared to conventional intraneural stimulation systems that only have a single electrode array (i.e., an intraneural electrode array). For example, one benefit of intraneural stimulation compared to intracochlear stimulation is improved selectivity. In other words, because the intraneural electrode contacts are in direct contact with the auditory nerve fibers, an intraneural stimulation system may more precisely stimulate a particular nerve fiber to convey a desired pitch. As a result, the pitch may be more accurately represented to the patient. However, selectivity comes at the cost of loudness. This is because an overly selectively stimulation strategy will not provide sufficient recruitment of nerve fibers to facilitate loudness growth. Hence, in order to represent relatively loud sounds, the intraneural stimulation system may have to apply a relatively high amount of stimulation current, which, in some cases, may be infeasible or disadvantageous in terms of battery life. Intracochlear stimulation, on the other hand, may not be as selective as intraneural stimulation, but it is relatively good at ensuring that a desired loudness growth is achieved.

Hence, in some examples, the intraneural stimulation system described herein may selectively represent audio content that has a sound level below a predetermined threshold by applying electrical stimulation representative of the audio content to the auditory nerve by way of the intraneural electrode array (i.e., by way of one or more intraneural electrode contacts disposed on the intraneural electrode array) and audio content that has a sound level above the predetermined threshold by applying electrical stimulation representative of the audio content to the auditory nerve by way of the intracochlear electrode array (i.e., by way of one or more intracochlear electrode contacts disposed on the intracochlear electrode array). In this manner, the benefits of both intraneural and intracochlear stimulation may be realized. Other benefits of having both an intraneural electrode array and an intracochlear electrode array in an intraneural stimulation system will be described in more detail below.

Figure 1:
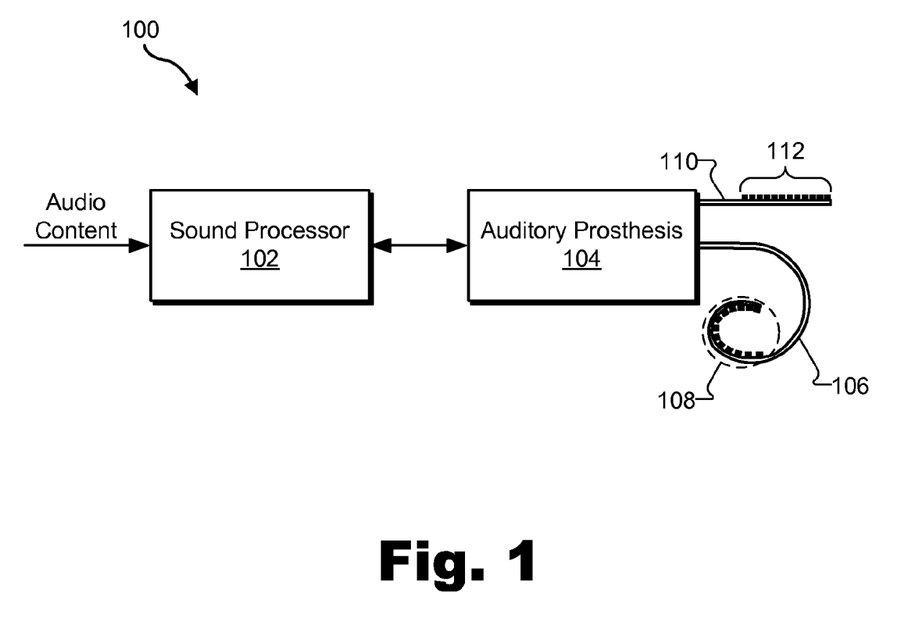
FIG. 1 illustrates an exemplary intraneural stimulation intraneural stimulation system according to principles described herein.

FIG. 1 illustrates an exemplary intraneural stimulation intraneural stimulation system 100. As shown, intraneural stimulation system 100 may include a sound processor 102, an auditory prosthesis 104, an intracochlear electrode array 106 having a plurality of intracochlear electrode contacts 108 disposed thereon, and an intraneural electrode array 110 having a plurality of intraneural electrode contacts 112 disposed thereon.

Sound processor 102 may include any suitable device configured to process audio content (e.g., one or more audio signals) presented to a patient and direct auditory prosthesis 104 to apply electrical stimulation representative of the audio content to the auditory nerve of the patient by way of intracochlear electrode array 106 and/or intraneural electrode array 110 (i.e., by way of one or more intracochlear electrode contacts 108 and/or intraneural electrode contacts 112. Sound processor 102 may be implemented by a behind-the-ear ("BTE") unit, a body worn device, a portable speech processor ("PSP"), an electro-acoustic stimulation device ("EAS device"), and/or any other type of sound processing unit as may serve a particular implementation.

Auditory prosthesis 104 may include any suitable auditory prosthesis configured to be at least partially implanted within a patient as may serve a particular implementation. For example, auditory prosthesis 104 may include a cochlear implant, a brainstem implant and/or any other type of auditory prosthesis. Sound processor 102 and auditory prosthesis 104 may communicate by way of any suitable wired or wireless communication channel.

Intracochlear electrode array 106 may be may be inserted into the cochlea of the patient such that intracochlear electrode contacts 108 are in communication with stimulation sites within the cochlea. In this configuration, sound processor 102 may direct auditory prosthesis 104 to apply electrical stimulation representative of an audio signal to one or more stimulation sites within the cochlea by way of one or more of intracochlear electrode contacts 108. As used herein, the term "in communication with" refers to intracochlear electrode contacts 108 being adjacent to, in the general vicinity of, in close proximity to, directly next to, or directly on the one or more stimulation sites. Any number of intracochlear electrode contacts 108 may be disposed on intracochlear electrode array 106 as may serve a particular implementation.

Figure 2:
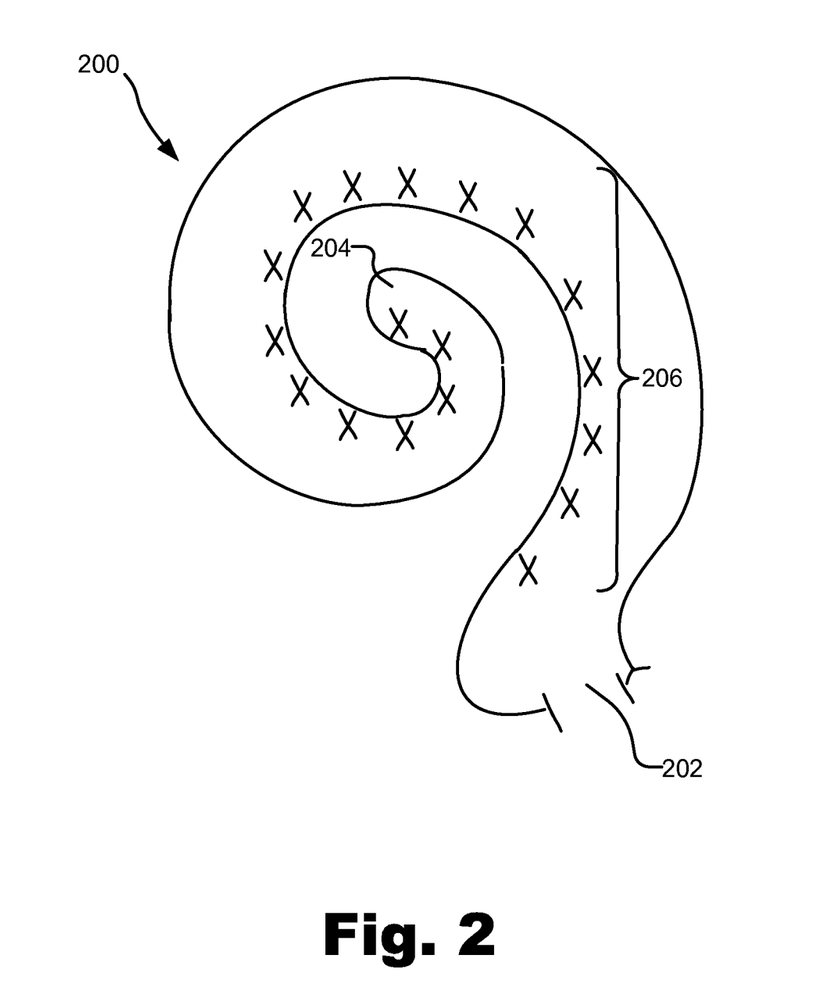
FIG. 2 illustrates a schematic structure of the human cochlea.

FIG. 2 illustrates a schematic structure of the human cochlea 200 into which intracochlear electrode array 106 may be inserted. As shown in FIG. 2, the cochlea 200 is in the shape of a spiral beginning at a base 202 and ending at an apex 204. Within the cochlea 200 resides auditory nerve tissue 206, which is denoted by Xs in FIG. 2. The auditory nerve tissue 206 is organized within the cochlea 200 in a tonotopic manner. Relatively low frequencies are encoded at or near the apex 204 of the cochlea 200 (referred to as an "apical region") while relatively high frequencies are encoded at or near the base 202 (referred to as a "basal region"). Hence, electrical stimulation applied by way of electrode contacts disposed within the apical region (i.e., "apical electrode contacts") may result in the patient perceiving relatively low frequencies and electrical stimulation applied by way of electrode contacts disposed within the basal region (i.e., "basal electrode contacts") may result in the patient perceiving relatively high frequencies. The delineation between the apical and basal electrode contacts on a particular electrode lead may vary depending on the insertion depth of the lead, the anatomy of the patient's cochlea, and/or any other factor as may serve a particular implementation.

Returning to FIG. 1, intraneural electrode array 110 may be inserted into the auditory nerve of the patient such that intraneural electrode contacts 112 are in communication with various nerve fibers included within the auditory nerve. In this configuration, sound processor 102 may direct auditory prosthesis 104 to apply electrical stimulation representative of an audio signal directly to one or more nerve fibers included within the auditory nerve by way of one or more of intraneural electrode contacts 112. Any number of intraneural electrode contacts 112 may be disposed on intraneural electrode array 110 as may serve a particular implementation. In some embodiments, the number of intraneural electrode contacts 112 is greater than the number of intracochlear electrode contacts 108. It will also be recognized that, in some embodiments, multiple intraneural electrode arrays 110 may be included in intraneural stimulation system 100. However, for illustrative purposes only, it will be assumed in the examples herein that only one intraneural electrode array 110 is included in intraneural stimulation system 100.

Figure 3:
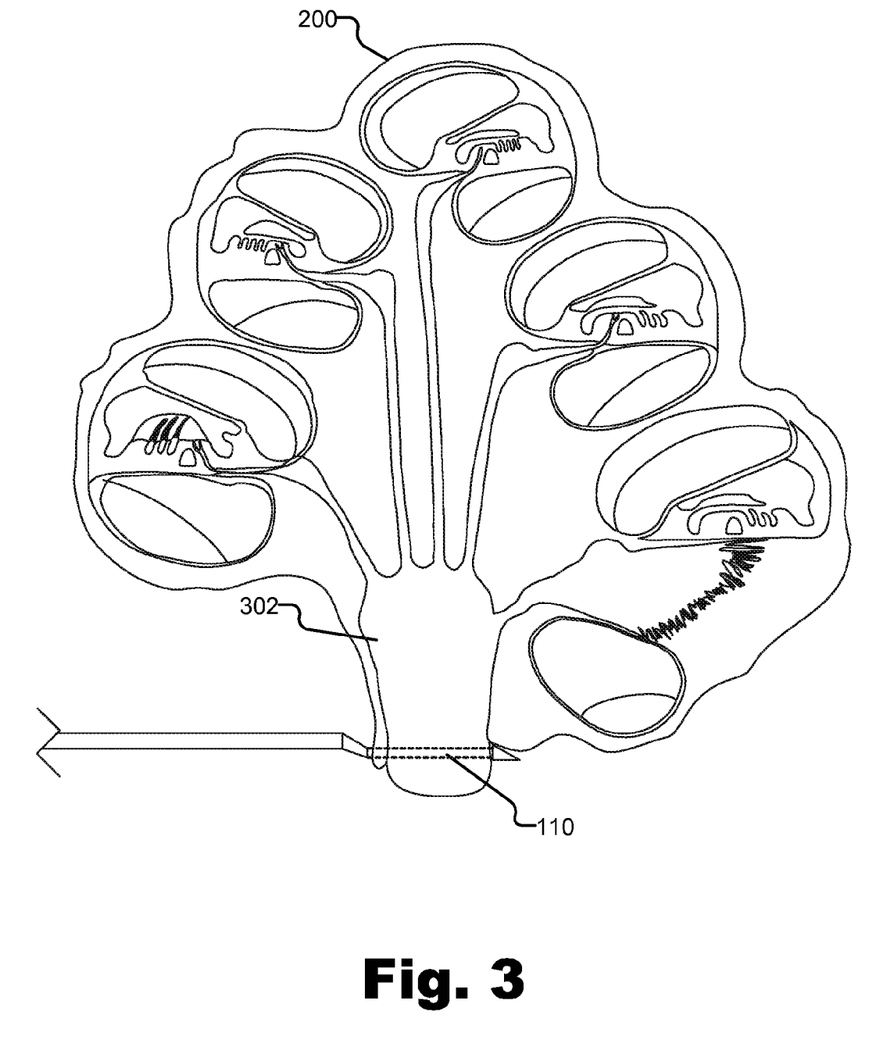
FIG. 3 shows an exemplary cross-sectional view of the human cochlea and the auditory nerve with an intraneural electrode array placed therein according to principles described herein.

FIG. 3 shows an exemplary cross-sectional view of the human cochlea 200 and the auditory nerve 302. As shown, the auditory nerve 302 exits the cochlea 200 at a base of the cochlea and forms a nerve bundle, or trunk. In some examples, intraneural electrode array 110 may be inserted into the trunk of the auditory nerve 302, as shown in FIG. 3. It will be recognized that intraneural electrode array 110 may be inserted into auditory nerve 302 at any other suitable location as may serve a particular implementation. It will also be recognized that any suitable insertion technique may be used to insert intraneural electrode array 110 into auditory nerve 302.

As mentioned, the auditory nerve comprises a nerve bundle (i.e., a bundle of individual nerve fibers each associated with a particular frequency range). Unfortunately, as mentioned above, the nerve fibers within the auditory nerve are organized helically. In other words, the relatively low frequency nerve fibers are located in the core of the auditory nerve and the relatively high frequency nerve fibers are located in the outer portion of the auditory nerve.

Hence, once a patient has been with intraneural stimulation system 100, and during follow-up test and checkups thereafter, it may be necessary to fit intraneural stimulation system 100 to the patient. Such "fitting" may include setting and/or adjustment of one or more control parameters governing an operation of intraneural stimulation system 100. For example, the fitting may include generating a frequency map for intraneural electrode array 110. In other words, the fitting may determine which intraneural electrode contacts 112 disposed on intraneural electrode array 110 correspond to which frequencies. Intraneural stimulation system 100 (i.e., sound processor 102) may then use the frequency map to determine which intraneural electrode contact 112 to stimulate in order to convey a particular pitch to the patient.

To facilitate fitting of intraneural stimulation system 100 to a patient, a fitting system may be selectively and communicatively coupled to intraneural stimulation system 100. As will be described below, the fitting system may additionally or alternatively be implemented by sound processor 102.

Figure 4:
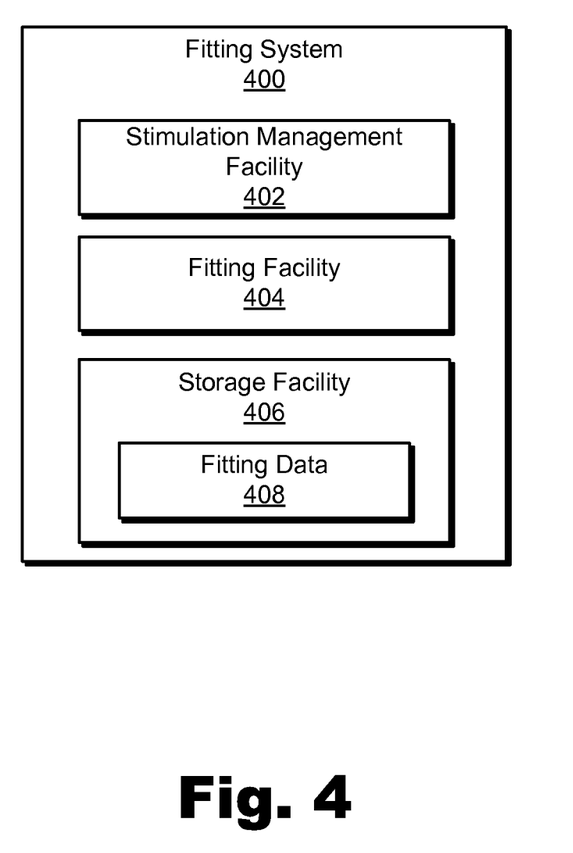
FIG. 4 illustrates an exemplary fitting system according to principles described herein.

FIG. 4 illustrates an exemplary fitting system 400 that may be used to fit an intraneural stimulation system (e.g., intraneural stimulation system 100) to a patient. As shown in FIG. 4, fitting system 400 may include a stimulation management facility 402, a fitting facility 404, and a storage facility 406, which may be in communication with one another using any suitable communication technologies. One or more of facilities 402-406 may include one or more computing devices and/or processors configured to perform one or more of the functions described herein. Facilities 402-406 will now be described in more detail.

Stimulation management facility 402 may be configured to perform one or more stimulation management operations. For example, in order to facilitate generation of a frequency map for an intraneural electrode array (e.g., intraneural electrode array 110), stimulation management facility 402 may direct an auditory prosthesis (e.g., auditory prosthesis 104) to apply electrical stimulation by way of a particular intracochlear electrode contact disposed on an intracochlear electrode array (e.g., intracochlear electrode array 106) that has been inserted into a cochlea of a patient. Stimulation management facility 402 may direct the auditory prosthesis to apply electrical stimulation by way of a particular intracochlear electrode contact in any suitable manner. For example, stimulation management facility 402 may transmit a command to a sound processor in communication with the auditory prosthesis directing the sound processor to direct the auditory prosthesis to apply the electrical stimulation. The electrical stimulation applied by way of the intracochlear electrode contact may have any suitable characteristic as may serve a particular implementation. For example, the electrical stimulation may include monopolar stimulation, multipolar (e.g., bipolar) stimulation, and/or any other type of stimulation as may serve a particular implementation.

Fitting facility 404 may be configured to perform one or more fitting operations associated with intraneural stimulation system 100. For example, fitting facility 404 may identify at least one intraneural electrode contact disposed on the intraneural electrode array that detects an evoked response that occurs in response to the application of the electrical stimulation by way of the intracochlear electrode contact. Fitting facility 404 may then designate the identified at least one intraneural electrode contact as being correlated with the intracochlear electrode contact and generate at least part of a frequency map for the intraneural electrode array based on the determined correlation.

Figure 5:
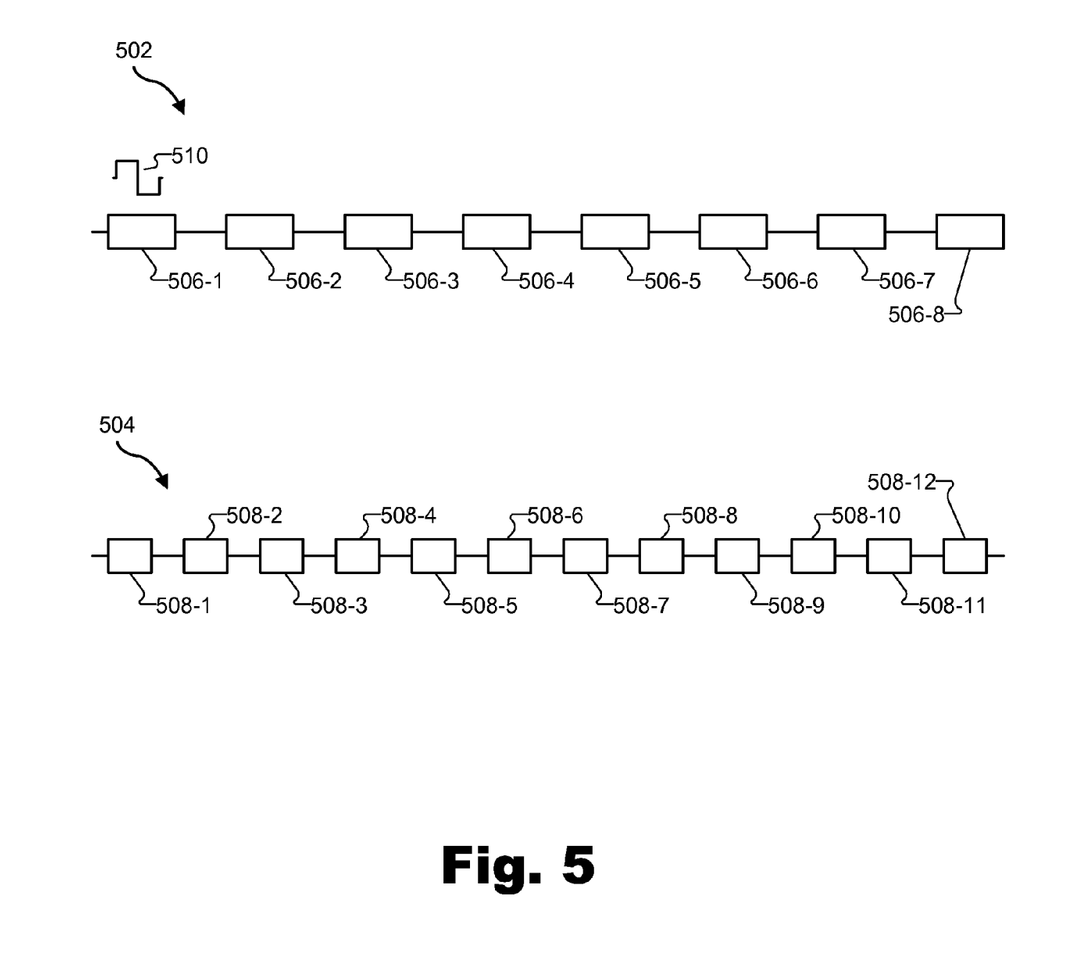
FIG. 5 shows an exemplary intracochlear electrode array and an exemplary intraneural electrode array according to principles described herein.

An example of generating a frequency map for an intraneural electrode array will be provided in connection with FIG. 5. FIG. 5 shows an exemplary intracochlear electrode array 502 and an exemplary intraneural electrode array 504 that may be included in a particular intraneural stimulation system. As shown, intracochlear electrode array 502 includes a plurality of intracochlear electrode contacts 506-1 through 506-8 (collectively referred to herein as "intracochlear electrode contacts 506") and intraneural electrode array 504 includes a plurality of intraneural electrode contacts 508-1 through 508-12 (collectively referred to herein as "intraneural electrode contacts 508"). The number of electrode contacts included in each electrode array 502 and 504 may vary as may serve a particular implementation.

Fitting facility 404 may generate a frequency map for intraneural electrode array 504 by determining which intraneural electrode contacts 508 correlate with which intracochlear electrode contacts 506. In other words, fitting facility 404 may determine which intraneural electrode contacts 508 and which intracochlear electrode contacts 506 correspond to the same frequencies.

To this end, fitting facility 404 may direct an auditory prosthesis to apply electrical stimulation by way of a particular intracochlear electrode contact 506. Each of the intraneural electrode contacts 508 may be directed to monitor for and record an evoked response that may occur in response to the application of the electrical stimulation. As used herein, an "evoked response" refers to a neural response (e.g., a compound action potential) and/or any other type of physiological response that may occur within a patient in response to application of electrical stimulation by way of an intracochlear electrode contact. Fitting facility 404 may then identify which of the intraneural electrode contacts 508 detects an evoked response that occurs in response to the application of the electrical stimulation and thereby determine that the identified intraneural electrode contact(s) are correlated with the intracochlear electrode contact.

For example, fitting facility 404 may direct the auditory prosthesis to apply a stimulation pulse 510 by way of intracochlear electrode contact 506-1. Intraneural electrode contact 508-12 may detect an evoked response that occurs in response to the application of stimulation pulse 510 by way of intracochlear electrode contact 506-1. Fitting facility 404 may then correlate intraneural electrode contact 508-12 with intracochlear electrode contact 506-1.

Figure 6:
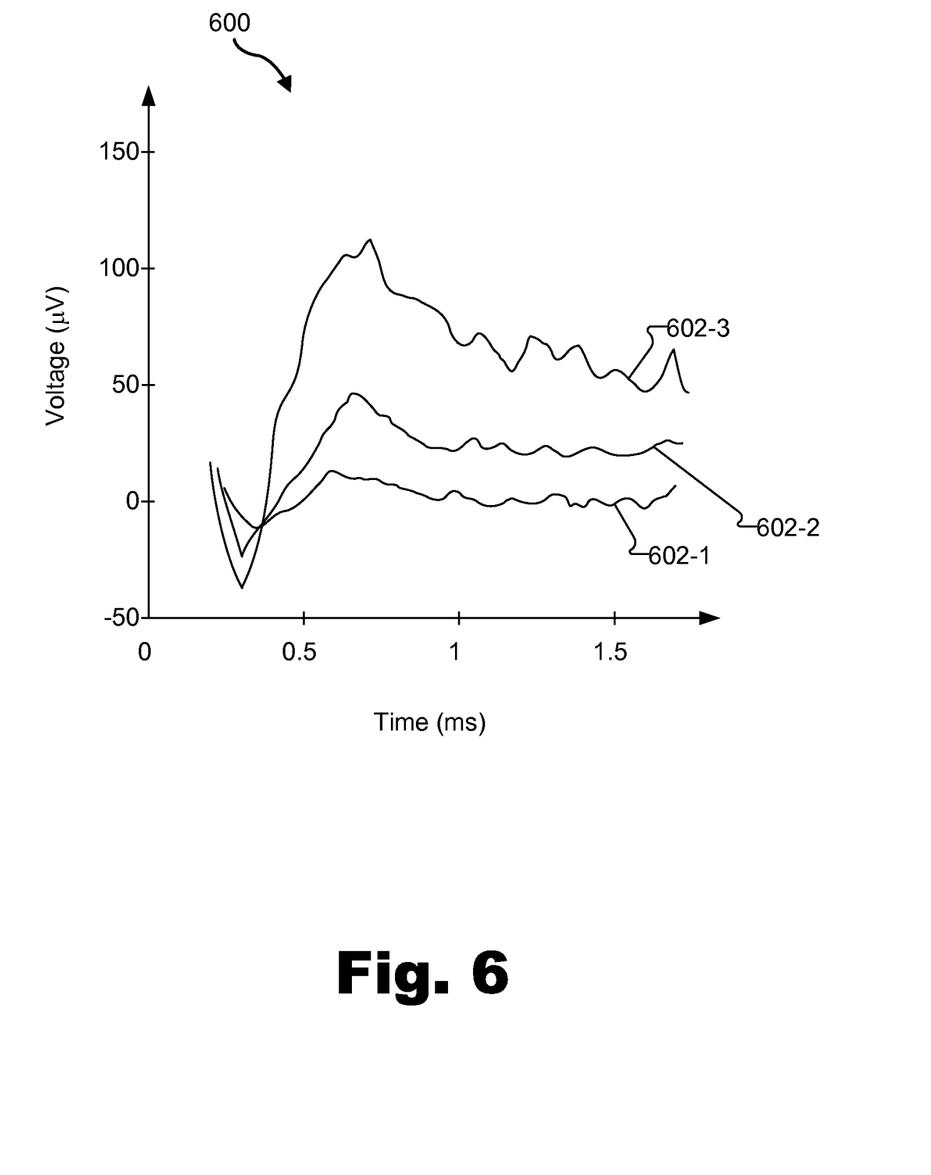
FIG. 6 shows a graph of evoked responses that may be detected by one or more intraneural electrode contacts according to principles described herein.

It will be recognized that multiple intraneural electrode contacts may detect an evoked response that occurs in response to application of electrical stimulation by way of a single intracochlear electrode contact. For example, intraneural electrode contacts 508-10 through 508-12 may detect an evoked response that occurs in response to application of electrical stimulation by way of intracochlear electrode contact 506-2. Fitting facility 404 may handle such an occurrence in any of a number of different ways. For example, fitting facility 404 may assign different degrees of correlation to each of the intraneural electrode contacts 508-10 through 508-12 based on the relative strengths of the evoked responses detected by each intraneural electrode contact. To illustrate, FIG. 6 shows a graph 600 of evoked responses 602-1 through 602-3 detected by intraneural electrode contacts 508-10, 508-11, and 508-12, respectively, in response to application of electrical stimulation by way of intracochlear electrode contact 506-2. As shown, the evoked response 602-3 detected by intraneural electrode contact 508-12 has an amplitude that is greater than the evoked responses 602-1 and 602-2 detected by intraneural electrode contacts 508-10 and 508-11. Intraneural electrode contact 508-12 may accordingly be assigned a relatively higher degree of correlation to intracochlear electrode contact 506-2 than intraneural electrode contacts 508-10 and 508-11.

Returning to FIG. 5, the process of applying electrical stimulation to intracochlear electrode contacts 506 and determining which intraneural electrode contacts 508 detect a resultant evoked response may be repeated for each of intracochlear electrode contacts 506. In this manner, degrees of correlation to each of the intracochlear electrode contacts 506 may be determined for many, if not all, of the intraneural electrode contacts 508. In some examples, one or more intraneural electrode contacts 508 may not be correlated with any of intracochlear electrode contacts 506. For example, for reasons described above, intracochlear electrode array 502 may not be inserted very deeply into the cochlea, thereby preventing any of the intracochlear electrode contacts 506 from being in communication with a low frequency stimulation site. Hence, one or more of the intraneural electrode contacts 508 that are in contact with low frequency neural fibers may not detect an evoked response that occurs in response to application of electrical stimulation to any of the intracochlear electrode contacts 506. Hence, in some examples, fitting facility 404 may deduce that the uncorrelated intraneural electrode contacts 508 correspond to relatively low frequencies.

Fitting facility 404 may utilize the determined correlations to generate a frequency map for intraneural electrode array 504. For example, intracochlear electrode contact 506-1 may correspond to (i.e., convey information representative of) a particular frequency range. If, as in the example described above, intraneural electrode contact 508-12 is correlated with intracochlear electrode contact 506-1, fitting facility 404 may assign intraneural electrode contact 508-12 to the same frequency range that corresponds to intracochlear electrode contact 506-1 and populate the frequency map with data representative of the assignment. Utilizing this data, intraneural stimulation system 100 may subsequently represent sounds having frequencies in the frequency range by applying electrical stimulation by way of intraneural electrode contact 508-12 and/or intracochlear electrode contact 506-1.

As another example, if varying degrees of correlation have been assigned to various intraneural electrode contacts 508, the different degrees of correlation may be processed (e.g., compared one to another) in order to assign distinct frequency ranges to each of intraneural electrode contacts 508. For example, intraneural electrode contacts 508-10 through 508-12 may have varying degrees of correlation with intracochlear electrode contact 506-2 as described above. For purposes of this example, intraneural electrode contact 508-10 may also have a relatively high degree of correlation with intracochlear electrode contact 506-3. Using this information, fitting facility 404 may determine that intraneural electrode contact 508-10 is associated with a frequency range that spans part of the frequency range associated with both intracochlear electrode contacts 506-2 and 506-3. For example, fitting facility 404 may assign a frequency range to intraneural electrode contact 508-10 that includes some of the lower frequencies included in the frequency range associated with intracochlear electrode contact 506-2 and some of the higher frequencies included in the frequency range associated with intracochlear electrode contact 506-3.

As another example, if a particular intraneural electrode contact (e.g., intraneural electrode contact 508-6) is not correlated with any of intracochlear electrode contacts 506, fitting facility 404 may determine that the intraneural electrode contact is in contact with a relatively low frequency nerve fiber and accordingly assign a relatively low frequency range to the intraneural electrode contact.

Additionally or alternatively, fitting facility 404 may determine which intraneural electrode contacts 508 correlate with which intracochlear electrode contacts 506 by directing an auditory prosthesis to apply electrical stimulation by way of a particular intracochlear electrode contact 508 and directing each of the intracochlear electrode contacts 506 to monitor for and record an evoked response that may occur in response to the application of the electrical stimulation. Fitting facility 404 may then identify which of the intracochlear electrode contacts 506 detects an evoked response that occurs in response to the application of the electrical stimulation and thereby determine that the identified intracochlear electrode contact(s) are correlated with the intraneural electrode contact.

It will be recognized that examples provided above are merely illustrative of the many different ways a frequency map may be automatically generated by fitting facility 404 for an intraneural electrode array. In some alternative embodiments, fitting facility 404 may be configured to generate a frequency map for an intraneural electrode array based on subjective feedback provided by the patient. For example, a clinician may utilize fitting facility 404 to perform a pitch matching exercise in which the patient is tasked with matching various pitches presented by way of the intracochlear electrode array and various pitches presented by way of the intraneural electrode array. Based on feedback provided by the patient, frequency ranges may be assigned to one or more of the intraneural electrode contacts.

To illustrate, referring again to FIG. 5, electrical stimulation may be sequentially applied by way of intracochlear electrode contact 506-1 and then by way of intraneural electrode contact 508-1. The patient may then be asked to compare the pitches of the sounds produced by the sequential stimulation. If the patient perceives the pitches as being identical, fitting facility 404 may designate intraneural electrode contact 508-1 as being correlated with intracochlear electrode contact 506-1. If the patient perceives the pitches as being different, the other intraneural electrode contacts 508 may be stimulated until a match is identified by the patient. This process may be repeated for each of the intracochlear electrode contacts 506 until a fitting map for intraneural electrode array 504 is generated.

Returning to FIG. 4, storage facility 406 may be configured to maintain fitting data 408 generated and/or utilized by stimulation management facility 402 and/or fitting facility 404. Storage facility 406 may be configured to maintain additional or alternative data as may serve a particular implementation.

Figure 7:
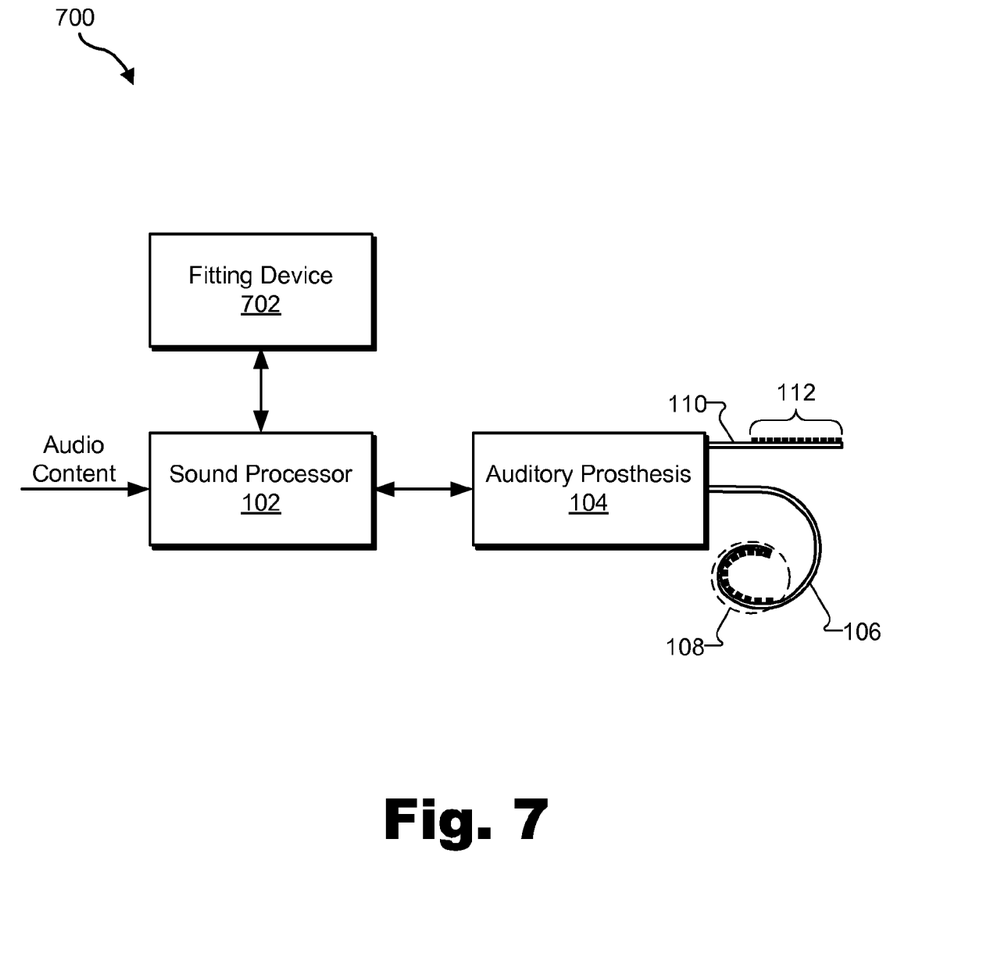
FIG. 7 shows an exemplary configuration in which the fitting system of FIG. 4 is at least partially implemented by a fitting device communicatively coupled to a sound processor according to principles described herein.

Fitting system 400 may be implemented by one or more components of intraneural stimulation 100. For example, fitting system 400 may be implemented entirely by sound processor 102. Alternatively, fitting system 400 may be at least partially implemented by a fitting device selectively and communicatively coupled to sound processor 102. To illustrate, FIG. 7 shows an exemplary configuration 700 in which fitting system 400 is at least partially implemented by a fitting device 702 communicatively coupled to sound processor 102. Fitting device 702 may implemented by any suitable combination of computing and communication devices including, but not limited to, a fitting station, a personal computer, a laptop computer, a handheld device, a mobile device (e.g., a mobile phone), and/or any other suitable component as may serve a particular implementation. In some examples, fitting device 702 may provide one or more graphical user interfaces ("GUIs") with which a clinician or other user may interface in order to fit intraneural stimulation system 100 to the patient.

Once intraneural stimulation system 100 has been fitted to a patient, intraneural stimulation system 100 may be used to provide electrical stimulation representative of audio content presented to the patient. The electrical stimulation may be applied by way of intracochlear electrode array 106 and/or intraneural electrode array 110. Various heuristics that may be used to determine which electrode array is to be used to provide the electrical stimulation will now be described.

In some examples, sound processor 102 may be configured to detect an auditory scene associated with the patient, select either the intracochlear electrode array 106 or the intraneural electrode array 110 (or, in some examples, both arrays 106 and 110) based on the detected auditory scene, and direct auditory prosthesis 104 to provide electrical stimulation representative of audio content presented to the patient by way of the selected electrode array. As used herein, an "auditory scene" associated with a patient refers to a particular auditory or listening environment of the patient. For example, an auditory scene may be representative of a scene in which the patient is listening primarily to music, a scene in which the patient is primarily listening to speech, a crowded restaurant, wind, noise from an airplane or automobile, a quiet bedroom, and/or any other auditory environment that the patient may experience.

For example, sound processor 102 may detect a particular auditory scene in which an expanded range of pitches that may be presented to a patient is desirable (e.g., an auditory scene in which the patient is listening primarily to music). In response, sound processor 102 may direct auditory prosthesis 104 to exclusively use intraneural electrode array 110 to apply electrical stimulation representative of audio content (e.g., music) presented to the patient while the patient is within the particular auditory scene. In this manner, intraneural stimulation system 100 may leverage the ability of intraneural electrode array 110 to convey relatively low pitches to the patient in order to provide a more accurate representation of the audio content to the patient.

Subsequently, sound processor 102 may detect a change in the auditory scene to an auditory scene in which an expanded range of pitches is relatively not so important (e.g., a change to an auditory scene in which the patient is listening primarily to speech). In response, sound processor 102 may direct auditory prosthesis 104 to exclusively use intracochlear electrode array 106 to apply electrical stimulation representative of audio content (e.g., speech) presented to the patient while the patient is within the particular auditory scene. In this manner, intracochlear stimulation system 100 may leverage the ability of intracochlear stimulation to accurately represent the audio content with relatively low levels of stimulation current (as compared to intraneural stimulation), thereby conserving battery life of auditory prosthesis 104.

As another example, sound processor 102 may select a particular electrode array based on the sound level of the audio content presented to the patient. For example, sound processor 102 may detect that a sound level of audio content presented to the patient is above a predetermined threshold. In response, sound processor 102 may select intracochlear electrode array 106 and direct auditory prosthesis 104 to apply electrical stimulation representative of the audio content to the auditory nerve by way of the selected intracochlear electrode array 106. In this manner, intraneural stimulation system 100 may leverage the ability of intracochlear stimulation to represent relatively loud audio content with relatively low levels of stimulation current (as compared to intraneural stimulation), thereby conserving battery life of auditory prosthesis 104. In some alternative embodiments, sound processor 102 may select, in response to detecting that the sound level is above the predetermined threshold, both intracochlear electrode array 106 and intraneural electrode array 110 and direct auditory prosthesis 104 to apply electrical stimulation representative of the audio content to the auditory nerve by way of both of the selected electrode arrays 106 and 110.

Conversely, sound processor 102 may select intraneural electrode array 110 if the sound level of the audio content presented to the patient is below the predetermined threshold. Sound processor 102 may then direct auditory prosthesis 104 to apply electrical stimulation representative of the audio content to the auditory nerve by way of the selected intraneural electrode array 110. In this manner, intraneural stimulation system 100 may leverage the selectivity that may be provided by intraneural stimulation in order to provide a more accurate representation of the audio content to the patient.

It will be recognized that the predetermined threshold to which the sound level of the audio content is compared may be determined in any suitable manner. For example, the predetermined threshold may be patient specific and may be determined by fitting facility 404 in accordance with any patient-specific factor as may serve a particular implementation. To illustrate, fitting facility 404 may determine a dynamic range of the patient and use the dynamic range to determine the predetermined threshold.

As another example, sound processor 102 may select a particular electrode array based on the frequency of the audio content presented to the patient. For example, sound processor 102 may detect that a frequency of audio content presented to the patient is greater than a predetermined threshold frequency. In response, sound processor 102 may select intracochlear electrode array 106 and direct auditory prosthesis 104 to apply electrical stimulation representative of the relatively high frequency audio content to the auditory nerve by way of the selected intracochlear electrode array 106. In this manner, intraneural stimulation system 100 may leverage the ability of intracochlear stimulation to accurately represent relatively high frequency audio content with relatively low levels of stimulation current (as compared to intraneural stimulation), thereby conserving battery life of auditory prosthesis 104.

Conversely, sound processor 102 may select intraneural electrode array 110 if the frequency of the audio content presented to the patient is less than the predetermined frequency threshold. Sound processor 102 may then direct auditory prosthesis 104 to apply electrical stimulation representative of the relatively low frequency audio content to the auditory nerve by way of the selected intraneural electrode array 110. In this manner, intraneural stimulation system 100 may leverage the ability of intraneural electrode array 110 to convey relatively low pitches to the patient in order to provide a more accurate representation of the audio content to the patient.

As another example, sound processor 102 may select a particular electrode array based on an amount of remaining battery life of auditory prosthesis 104. For example, sound processor 102 may detect that an amount of remaining battery life of auditory prosthesis 104 is below a predetermined threshold level. In response, sound processor 102 may select intracochlear electrode array 106 and direct auditory prosthesis 104 to apply electrical stimulation representative of audio content presented to the patient by way of the selected intracochlear electrode array 106. In this manner, intraneural stimulation system 100 may leverage the relatively low power consumption requirements associated with intracochlear stimulation in order to conserve battery life of auditory prosthesis 104.

Conversely, sound processor 102 may select intraneural electrode array 110 if the amount of remaining battery life of auditory prosthesis 104 is above a predetermined threshold level. Sound processor 102 may then direct auditory prosthesis 104 to apply electrical stimulation representative of the audio content presented to the patient by way of the selected intraneural electrode array 110. In this manner, intraneural stimulation system 100 may leverage the selectivity that may be provided by intraneural stimulation in order to provide a more accurate representation of the audio content to the patient.

As another example, sound processor 102 may select a particular electrode array based on a manual selection of a particular stimulation mode. The manual selection of the particular stimulation mode may be performed by the patient, a clinician, or any other user.

To illustrate, sound processor 102 may detect a manual selection of a particular stimulation mode that utilizes only intracochlear stimulation. In response, sound processor 102 may direct auditory prosthesis 104 to apply electrical stimulation representative of audio content presented to the patient to the auditory nerve by way of intracochlear electrode array 106. Likewise, if sound processor 102 detects a manual selection of a particular stimulation mode that utilizes only intraneural stimulation, sound processor 102 may direct auditory prosthesis 104 to apply electrical stimulation representative of audio content presented to the patient by way of intraneural electrode array 110.

In some examples, intraneural stimulation system 100 may be deployed in an EAS configuration configured to provide both electrical and acoustic stimulation to a patient. For example, electrical stimulation may be used to represent relatively high frequencies and acoustic stimulation may be used to represent relatively low frequencies. In some examples, the acoustic stimulation may be provided by way of an acoustic stimulation element (e.g., a loudspeaker, receiver, an apparatus that provides sound vibration to the middle and/or inner ear, etc.) communicatively coupled to sound processor 102. Additionally or alternatively, the acoustic stimulation may be provided by way of an electromechanical transducer coupled to the cochlea and/or integrated into intracochlear electrode array 106.

Additionally or alternatively, intraneural stimulation system 100 may be deployed in a binaural configuration (i.e., a configuration in which electrical stimulation is presented to both ears of the patient). In this configuration, specially designed coding strategies may be used to activate the binaural pathways passing through the medial superior olive ("MSO") in response to stimulation of the auditory nerve on both sides of the patient. In this manner, improved binaural performance and spatial hearing may be achieved.

Additionally or alternatively, intraneural stimulation system 100 may be further configured to facilitate optical stimulation of the cochlea and/or auditory nerve. For example, one or more optical stimulation elements (e.g., diodes, waveguides, etc.) may be disposed on intracochlear electrode array 106 and/or intraneural electrode array 110. Intraneural stimulation system 100 may be configured to provide optical stimulation by way of the one or more optical stimulation elements. In some examples, combining optical stimulation with intracochlear and/or intraneural electrical stimulation may augment the selectivity of intraneural stimulation system 100.

Figure 8:
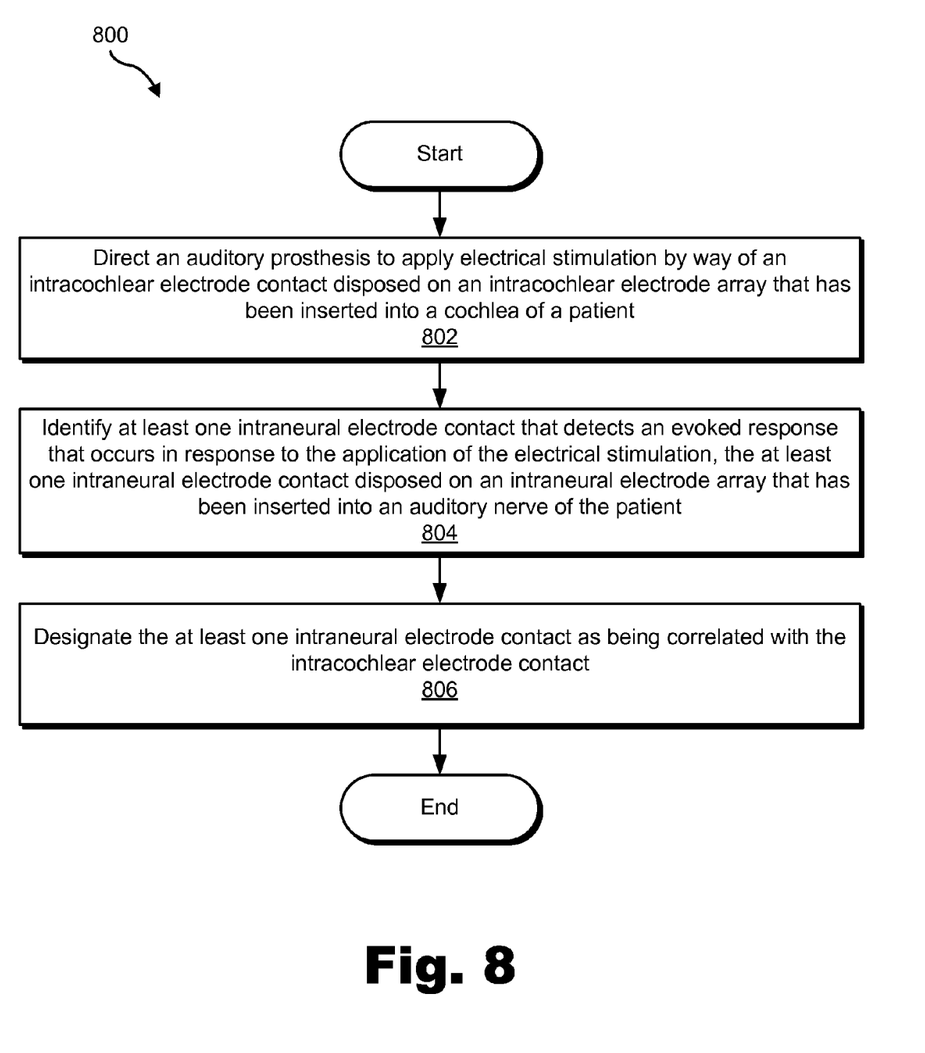
FIG. 8 illustrates an exemplary method of fitting an intraneural stimulation system that includes both an intracochlear electrode array and an intraneural electrode array to a patient according to principles described herein.

FIG. 8 illustrates an exemplary method 800 of fitting an intraneural stimulation system that includes both an intracochlear electrode array and an intraneural electrode array to a patient. While FIG. 8 illustrates exemplary steps according to one embodiment, other embodiments may omit, add to, reorder, and/or modify any of the steps shown in FIG. 8. One or more of the steps shown in FIG. 8 may be performed by fitting system 400 and/or any implementation thereof.

In step 802, a fitting system directs an auditory prosthesis to apply electrical stimulation by way of an intracochlear electrode contact disposed on an intracochlear electrode array that has been inserted into a cochlea of a patient. Step 802 may be performed in any of the ways described herein.

In step 804, the fitting system identifies at least one intraneural electrode contact that detects an evoked response that occurs in response to the application of the electrical stimulation, the at least one intraneural electrode contact disposed on an intraneural electrode array that has been inserted into an auditory nerve of the patient. Step 804 may be performed in any of the ways described herein.

In step 806, the fitting system designates the at least one intraneural electrode contact as being correlated with the intracochlear electrode contact. Step 806 may be performed in any of the ways described herein.

In certain embodiments, one or more of the processes described herein may be implemented at least in part as instructions embodied in a non-transitory computer-readable medium and executable by one or more computing devices. In general, a processor (e.g., a microprocessor) receives instructions, from a non-transitory computer-readable medium, (e.g., a memory, etc.), and executes those instructions, thereby performing one or more processes, including one or more of the processes described herein. Such instructions may be stored and/or transmitted using any of a variety of known computer-readable media.

A computer-readable medium (also referred to as a processor-readable medium) includes any non-transitory medium that participates in providing data (e.g., instructions) that may be read by a computer (e.g., by a processor of a computer). Such a medium may take many forms, including, but not limited to, non-volatile media, and/or volatile media. Non-volatile media may include, for example, optical or magnetic disks and other persistent memory. Volatile media may include, for example, dynamic random access memory ("DRAM"), which typically constitutes a main memory. Common forms of computer-readable media include, for example, a disk, hard disk, magnetic tape, any other magnetic medium, a CD-ROM, DVD, any other optical medium, a RAM, a PROM, an EPROM, a FLASH-EEPROM, any other memory chip or cartridge, or any other tangible medium from which a computer can read.

Figure 9:
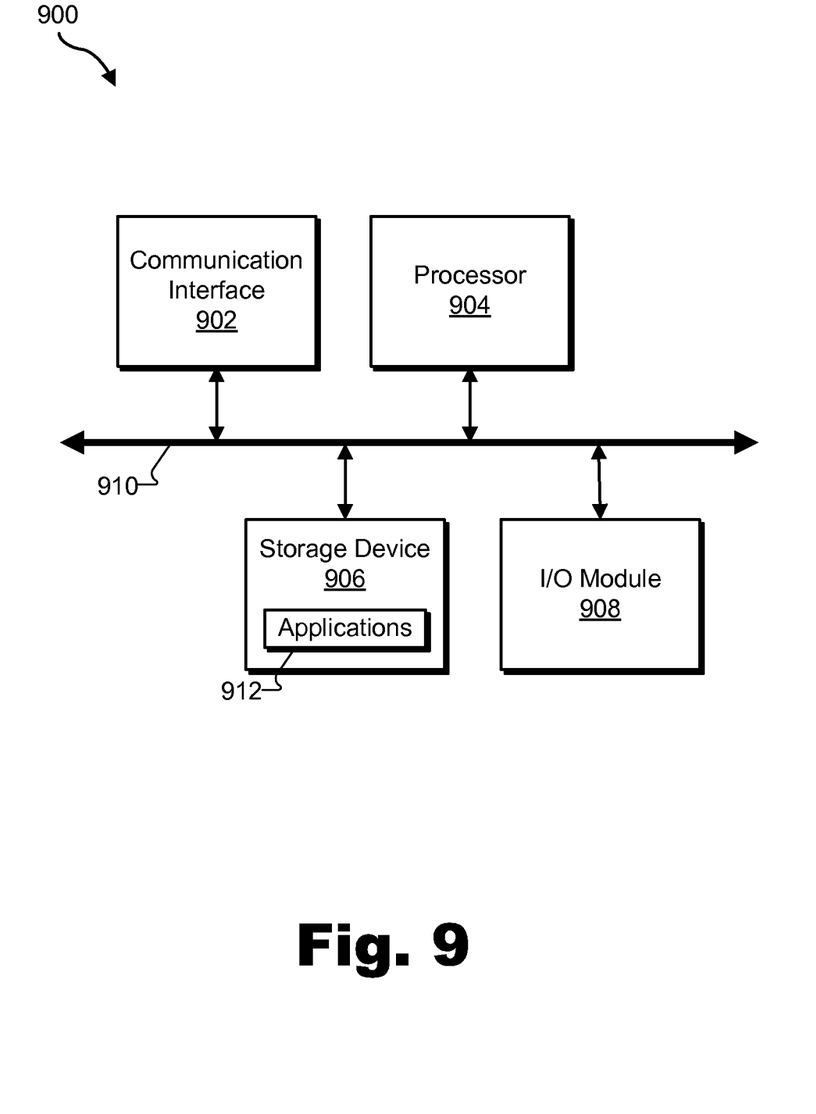
FIG. 9 illustrates an exemplary computing device according to principles described herein.

FIG. 9 illustrates an exemplary computing device 900 that may be configured to perform one or more of the processes described herein. As shown in FIG. 9, computing device 900 may include a communication interface 902, a processor 904, a storage device 906, and an input/output ("I/O") module 908 communicatively connected via a communication infrastructure 910. While an exemplary computing device 900 is shown in FIG. 9, the components illustrated in FIG. 9 are not intended to be limiting. Additional or alternative components may be used in other embodiments. Components of computing device 900 shown in FIG. 9 will now be described in additional detail.

Communication interface 902 may be configured to communicate with one or more computing devices. Examples of communication interface 902 include, without limitation, a wired network interface (such as a network interface card), a wireless network interface (such as a wireless network interface card), a modem, an audio/video connection, and any other suitable interface.

Processor 904 generally represents any type or form of processing unit capable of processing data or interpreting, executing, and/or directing execution of one or more of the instructions, processes, and/or operations described herein. Processor 904 may direct execution of operations in accordance with one or more applications 912 or other computer-executable instructions such as may be stored in storage device 906 or another computer-readable medium.

Storage device 906 may include one or more data storage media, devices, or configurations and may employ any type, form, and combination of data storage media and/or device. For example, storage device 906 may include, but is not limited to, a hard drive, network drive, flash drive, magnetic disc, optical disc, random access memory ("RAM"), dynamic RAM ("DRAM"), other non-volatile and/or volatile data storage units, or a combination or sub-combination thereof. Electronic data, including data described herein, may be temporarily and/or permanently stored in storage device 906. For example, data representative of one or more executable applications 912 configured to direct processor 904 to perform any of the operations described herein may be stored within storage device 906. In some examples, data may be arranged in one or more databases residing within storage device 906.

I/O module 908 may be configured to receive user input and provide user output and may include any hardware, firmware, software, or combination thereof supportive of input and output capabilities. For example, I/O module 908 may include hardware and/or software for capturing user input, including, but not limited to, a keyboard or keypad, a touch screen component (e.g., touch screen display), a receiver (e.g., an RF or infrared receiver), and/or one or more input buttons.

I/O module 908 may include one or more devices for presenting output to a user, including, but not limited to, a graphics engine, a display (e.g., a display screen, one or more output drivers (e.g., display drivers), one or more audio speakers, and one or more audio drivers. In certain embodiments, I/O module 908 is configured to provide graphical data to a display for presentation to a user. The graphical data may be representative of one or more graphical user interfaces and/or any other graphical content as may serve a particular implementation.

In some examples, any of the facilities described herein may be implemented by or within one or more components of computing device 900. For example, one or more applications 912 residing within storage device 906 may be configured to direct processor 904 to perform one or more processes or functions associated with any of the facilities and/or systems described herein.

In the preceding description, various exemplary embodiments have been described with reference to the accompanying drawings. It will, however, be evident that various modifications and changes may be made thereto, and additional embodiments may be implemented, without departing from the scope of the invention as set forth in the claims that follow. For example, certain features of one embodiment described herein may be combined with or substituted for features of another embodiment described herein. The description and drawings are accordingly to be regarded in an illustrative rather than a restrictive sense.

What is claimed is:

1. A system comprising:
    an auditory prosthesis configured to be implanted within a patient;
    an intracochlear electrode array communicatively coupled to the auditory prosthesis and configured to be inserted into a cochlea of the patient;
    an intraneural electrode array communicatively coupled to the auditory prosthesis and configured to be inserted into an auditory nerve of the patient; and
    a sound processor communicatively coupled to the auditory prosthesis and configured to direct the auditory prosthesis to stimulate the auditory nerve by applying electrical stimulation by way of at least one of the intracochlear electrode array and the intraneural electrode array.

2. The system of claim 1, further comprising a fitting system selectively and communicatively coupled to the auditory prosthesis, the fitting system configured to
    direct the auditory prosthesis to apply electrical stimulation by way of an intracochlear electrode contact disposed on the intracochlear electrode array;
    identify at least one intraneural electrode contact that detects an evoked response that occurs in response to the application of the electrical stimulation, the at least one intraneural electrode contact disposed on the intraneural electrode array, and
    designate the at least one intraneural electrode contact as being correlated with the intracochlear electrode contact.

3. The system of claim 2, wherein the fitting system is further configured to generate at least part of a frequency map for the intraneural electrode array based on the correlation between the at least one intraneural electrode contact and the intracochlear electrode contact.

4. The system of claim 1, further comprising a fitting system selectively and communicatively coupled to the auditory prosthesis, the fitting system configured to
    direct the auditory prosthesis to apply electrical stimulation by way of an intraneural electrode contact disposed on the intraneural electrode array;
    identify at least one intracochlear electrode contact that detects an evoked response that occurs in response to the application of the electrical stimulation, the at least one intracochlear electrode contact disposed on the intracochlear electrode array, and
    designate the at least one intracochlear electrode contact as being correlated with the intraneural electrode contact.

5. The system of claim 1, further comprising a fitting system selectively and communicatively coupled to the auditory prosthesis and configured to generate the at least part of a frequency map for the intraneural electrode array based on subjective feedback provided by the patient.

6. The system of claim 1, wherein the sound processor is further configured to:
   detect an auditory scene associated with the patient;
   select one of the intracochlear electrode array and the intraneural electrode array based on the detected auditory scene; and
   direct the auditory prosthesis to stimulate the auditory nerve by applying electrical stimulation by way of the selected electrode array.

7. The system of claim 1, wherein the sound processor is further configured to:
   detect an auditory scene associated with the patient;
   select both the intracochlear electrode array and the intraneural electrode array based on the detected auditory scene; and
   direct the auditory prosthesis to stimulate the auditory nerve by applying electrical stimulation by way of both of the selected electrode arrays.

8. The system of claim 1, wherein the sound processor is further configured to:
   detect that a sound level of audio content presented to the patient is above a predetermined threshold;
   select the intracochlear electrode array in response to detecting that the sound level is above the predetermined threshold; and
   direct the auditory prosthesis to apply electrical stimulation representative of the audio content to the auditory nerve by way of the selected intracochlear electrode array.

9. The system of claim 1, wherein the sound processor is further configured to:
   detect that a sound level of audio content presented to the patient is above a predetermined threshold;
   select both the intracochlear electrode array and the intraneural electrode array in response to detecting that the sound level is above the predetermined threshold; and
   direct the auditory prosthesis to apply electrical stimulation representative of the audio content to the auditory nerve by way of both of the selected electrode arrays.

10. The system of claim 1, wherein the sound processor is further configured to:
    detect that a sound level of audio content presented to the patient is below a predetermined threshold;
    select the intraneural electrode array in response to detecting that the sound level is below the predetermined threshold; and
    direct the auditory prosthesis to apply electrical stimulation representative of the audio content to the auditory nerve by way of the selected intraneural electrode array.

11. The system of claim 1, wherein the sound processor is further configured to:
    detect that a frequency of audio content presented to the patient is greater than a predetermined threshold frequency;
    select the intracochlear electrode array in response to detecting that the frequency of the audio content is greater than the predetermined threshold frequency; and
    direct the auditory prosthesis to apply electrical stimulation representative of the audio content to the auditory nerve by way of the selected intracochlear electrode array.

12. The system of claim 1, wherein the sound processor is further configured to:
    detect that a frequency of audio content presented to the patient is less than a predetermined threshold frequency;
    select the intraneural electrode array in response to detecting that the frequency of the audio content is less than the predetermined threshold frequency; and
    direct the auditory prosthesis to apply electrical stimulation representative of the audio content to the auditory nerve by way of the selected intraneural electrode array.

13. The system of claim 1, wherein the sound processor is further configured to:
    detect that an amount of remaining of battery life of the auditory prosthesis is below a predetermined threshold level;
    select the intracochlear electrode array in response to detecting that the remaining amount of battery life is below the predetermined threshold level; and
    direct the auditory prosthesis to apply electrical stimulation representative of the audio content to the auditory nerve by way of the selected intracochlear electrode array.

14. The system of claim 1, wherein the sound processor is further configured to:
    detect that an amount of remaining of battery life of the auditory prosthesis is above a predetermined threshold level;
    select the intraneural electrode array in response to detecting that the remaining amount of battery life is above the predetermined threshold level; and
    direct the auditory prosthesis to apply electrical stimulation representative of the audio content to the auditory nerve by way of the selected intraneural electrode array.

15. The system of claim 1, wherein the sound processor is further configured to:
    detect a manual selection of a particular stimulation mode that utilizes only intracochlear stimulation; and
    direct, in response to the manual selection of the particular stimulation mode, the auditory prosthesis to apply electrical stimulation representative of audio content presented to the patient to the auditory nerve by way of the intracochlear electrode array.

16. The system of claim 1, wherein the sound processor is further configured to:
    detect a manual selection of a particular stimulation mode that utilizes only intraneural stimulation; and
    direct, in response to the manual selection of the particular stimulation mode, the auditory prosthesis to apply electrical stimulation representative of audio content presented to the patient to the auditory nerve by way of the intraneural electrode array.

17. The system of claim 1, further comprising:
    an acoustic stimulation element communicatively coupled to the sound processor;
    wherein the sound processor is further configured to apply acoustic stimulation to the patient by way of the acoustic stimulation element.

18. The system of claim 1, further comprising one or more optical stimulation elements disposed on at least one of the intracochlear electrode array and the intraneural electrode array.

19. A system comprising:
    a stimulation management facility configured to direct an auditory prosthesis to apply electrical stimulation by way of an intracochlear electrode contact disposed on an intracochlear electrode array that has been inserted into a cochlea of a patient; and
    a fitting facility communicatively coupled to the stimulation management facility and configured to
    identify at least one intraneural electrode contact that detects an evoked response that occurs in response to the application of the electrical stimulation, the at least one intraneural electrode contact disposed on an intraneural electrode array that has been inserted into an auditory nerve of the patient, and designate the at least one intraneural electrode contact as being correlated with the intracochlear electrode contact.

20. The system of claim 19, wherein the fitting facility is further configured to generate at least part of a frequency map for the intraneural electrode array based on the correlation between the at least one intraneural electrode contact and the intracochlear electrode contact.

21. A method comprising:

directing, by a fitting system, an auditory prosthesis to apply electrical stimulation by way of an intracochlear electrode contact disposed on an intracochlear electrode array that has been inserted into a cochlea of a patient;

identifying, by the fitting system, at least one intraneural electrode contact that detects an evoked response that occurs in response to the application of the electrical stimulation, the at least one intraneural electrode contact disposed on an intraneural electrode array that has been inserted into an auditory nerve of the patient;

designating, by the fitting system, the at least one intraneural electrode contact as being correlated with the intracochlear electrode contact; and generating, by the fitting system, at least part of a frequency map for the intraneural electrode array based on the correlation between the at least one intraneural electrode contact and the intracochlear electrode contact.

* * * * *